US012642765B2

(12) United States Patent
Sudhakar et al.

(10) Patent No.: US 12,642,765 B2
(45) Date of Patent: Jun. 2, 2026

(54) ATOMOXETINE ORAL SOLUTION

(71) Applicant: OWP Pharmaceuticals, Inc., Naperville, IL (US)

(72) Inventors: Paul Sudhakar, Shawnee, KS (US); Scott Boyer, West Chicago, IL (US)

( * ) Notice: Subject to any disclaimer, the term of this patent is extended or adjusted under 35 U.S.C. 154(b) by 234 days.

(21) Appl. No.: 18/532,721

(22) Filed: Dec. 7, 2023

(65) Prior Publication Data

US 2024/0197631 A1 Jun. 20, 2024

Related U.S. Application Data

(60) Provisional application No. 63/386,449, filed on Dec. 7, 2022.

(51) Int. Cl.

| | |
|---|---|
| ***A61K 9/08*** | (2006.01) |
| ***A61K 9/00*** | (2006.01) |
| ***A61K 31/138*** | (2006.01) |
| ***A61K 47/10*** | (2017.01) |
| ***A61K 47/12*** | (2006.01) |
| ***A61K 47/14*** | (2017.01) |
| ***A61K 47/26*** | (2006.01) |
| ***A61K 47/36*** | (2006.01) |
| ***A61K 47/46*** | (2006.01) |

(52) U.S. Cl.

CPC .............. *A61K 9/08* (2013.01); *A61K 9/0053* (2013.01); *A61K 31/138* (2013.01); *A61K 47/10* (2013.01); *A61K 47/12* (2013.01); *A61K 47/14* (2013.01); *A61K 47/26* (2013.01); *A61K 47/36* (2013.01); *A61K 47/46* (2013.01)

(58) Field of Classification Search

CPC ...... A61K 9/08; A61K 9/0053; A61K 31/138; A61K 47/10; A61K 47/12; A61K 47/14; A61K 47/26; A61K 47/36; A61K 47/46

See application file for complete search history.

(56) References Cited

FOREIGN PATENT DOCUMENTS

| | | | | |
|---|---|---|---|---|
| EP | 0052492 B1 | | 2/1984 | |
| WO | WO-2015144255 A1 | * | 10/2015 | ........... A61K 31/135 |

* cited by examiner

*Primary Examiner* — Quanglong N Truong

(74) *Attorney, Agent, or Firm* — Carlson, Caspers, Vandenburgh & Lindquist, P.A.

(57) ABSTRACT

The present invention provides for an oral solution that includes atomoxetine, or pharmaceutically acceptable salt thereof, methods of manufacturing the oral solution, and methods of treating attention deficit hyperactivity disorder (ADHD) in a human subject that include orally administering the oral solution to a human subject in need thereof.

21 Claims, No Drawings

ATOMOXETINE ORAL SOLUTION

Atomoxetine is a highly selective and potent inhibitor of the pre-synaptic noradrenaline transporter, its presumed mechanism of action, without directly affecting the serotonin or dopamine transporters and it is 2 and 9 times more effective than the racemic mixture and the (+)-enantiomer, respectively, of N-methyl-3-(2-methylphenoxy)-3-phenylpropylamine (tomoxetine), disclosed in EP0052492. Atomoxetine is the (R)-(−) enantiomer of tomoxetine.

The hydrogen chloride salt of atomoxetine, atomoxetine HCl, is marketed as Strattera®, which is prescribed as oral capsules having dosages of 10 mg, 18 mg, 25 mg, 40 mg, and 60 mg for the treatment of attention deficit hyperactivity disorder (ADHD), in children over 6 years of age and adults.

Although oral solid dosage forms such as capsules are very popular for reasons that are mainly due to ease of management, for certain users (e.g., children and the elderly) these forms are not necessarily a convenient option, especially due to difficulty in swallowing these forms. This lack of convenience results in a high incidence of non-compliance and ineffective therapy. Moreover, the Prescribing Information of Strattera® capsules discloses a dosing scheme for children over 6 years of age and adolescents up to 70 kg according to which dosing is adjusted to their body weight whereas the corresponding adult-dosing is subjected to titration dependent on their response.

An atomoxetine oral solution (4 milligrams per milliliter [mg/mL]) is known to have been in the subject of a Bioequivalence study in healthy adult male Japanese subjects, organized by Eli Lilly in 2010. However, as a means of both ensuring flexibility in dose titration and advanced patient compliance, the development of oral pharmaceutical solutions with higher concentrations of atomoxetine hydrochloride which can allow smaller dose is definitely an existing need.

Although atomoxetine hydrochloride is soluble in water (27.8 mg/ml at room temperature) the desire for the development of a high concentrated oral solution dosage form of atomoxetine hydrochloride is complicated by the fact that it is extremely bitter tasting.

Thus, it is challenging to formulate an atomoxetine hydrochloride solution especially at high concentrations since it is generally considered difficult to effectively taste mask the bitterness in concentrated liquid dosage forms.

SUMMARY OF THE INVENTION

The present invention provides for an oral solution that includes: (i) atomoxetine, or pharmaceutically acceptable salt thereof; (ii) antimicrobial preservative that includes methylparaben and sodium benzoate; (iii) buffering agent that includes citric acid and trisodium citrate dihydrate; (iv) sweetening agent that includes sucralose and sorbitol; (v) solvent that includes water, propylene glycol, and glycerin; (vi) optionally flavoring agent that includes cherry flavor; and (vii) optionally coloring agent that includes FD & C Red No. 40 and Allura Red AC.

The present invention also provides for an oral solution that includes: (i) 11.43±3 mg/mL atomoxetine hydrochloride; (ii) antimicrobial preservative that includes 1±0.2 mg/mL methylparaben and 1±0.2 mg/mL sodium benzoate; (iii) buffering agent that includes 1.50±0.3 mg/mL citric acid and 1.34±0.27 mg/mL trisodium citrate dihydrate; (iv) sweetening agent that includes 1 mg/mL sucralose and 56.25±11 mg/mL sorbitol; (v) solvent that includes 811.70±50 mg/mL water, 20±4 mg/mL propylene glycol, and 75±15 mg/mL glycerin; (vi) flavoring agent that includes 2±0.4 mg/mL cherry flavor; and (vii) coloring agent that includes 0.001±0.0002 mg/mL FD & C Red No. 40 and 0.001±0.0002 mg/mL Allura Red AC.

The present invention also provides for a method of treating attention deficit hyperactivity disorder (ADHD) in a human subject. The method includes orally administering the oral solution described herein to a human subject in need thereof, in an amount and for a period of time sufficient to treat ADHD.

DETAILED DESCRIPTION OF THE INVENTION

The present invention can be more readily understood by reading the following detailed description of the invention and study of the included examples.

As used herein, the following terms have the meaning ascribed to them unless specified otherwise.

The terms "comprise," "comprising," "include," "including," and "includes" when used in this specification and claims are intended to specify the presence of stated substances, features, integers, components, or steps, but they do not preclude the presence or addition of one or more other substances, features, integers, components, steps, or combinations thereof.

The articles "a" and "an" as used herein refer to "one or more" or "at least one," unless otherwise indicated. That is, reference to any element or component of an embodiment by the indefinite article "a" or "an" does not exclude the possibility that more than one element or component is present.

The term "atomoxetine" refers to the compound with the chemical name (R)—N-methyl-3-phenyl-3-(o-tolyloxy)propan-1-amine; CAS number 83015-26-3 (82248-59-7 as the HCl); formula $C_{17}H_{21}NO$; molar mass 255.361 g·mol$^{-1}$; and chemical structure shown below.

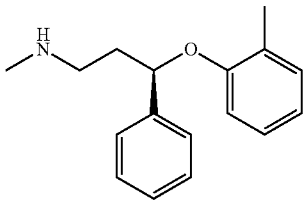 [SMILES: CNCC[C@@H](Oc1ccccc1C)c1ccccc1]

Atomoxetine can exist as the free base, or as a pharmaceutically acceptable salt thereof (e.g., as the hydrochloride salt).

The term "pharmaceutically acceptable" refers to those compounds, excipients, active ingredients, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

As used herein, "buffer" or "buffering agent" refers to a substance capable of keeping the pH at a nearly constant value in a wide variety of chemical applications. Typically, the buffer consists of a mixture of a weak acid and its conjugate base, or vice versa. Buffers suitable in the manufacture of the oral solution described herein include citric acid, anhydrous and trisodium citrate, dihydrate.

As used herein, "sweetener" or "sweetening agent" refers to a substance that when added to the oral solution, imparts the flavor of sweetness, either because it contains a type of sugar, or because it contains a sweet-tasting sugar substitute. Sweeteners suitable in the manufacture of the oral solution described herein include sucralose and sorbitol. The sorbitol can be, e.g., sorbitol solution, 70 percent.

As used herein, "preservative" or "antimicrobial preservative" refers to a substance that when added to the oral solution, prevents, or mitigates decomposition by microbial growth or by undesirable chemical changes. Preservatives suitable in the manufacture of the oral solution described herein include sodium benzoate, powder and methylparaben, powder.

As used herein, "colorant" or "coloring agent" refers to a substance that is added in order to change the color of the oral solution. One colorant suitable in the manufacture of the oral solution described herein is FD&C Red No. 40.

As used herein, "flavor" or "flavoring agent" refers to a substance that is added to improve the taste or smell of the oral solution. One flavor suitable in the manufacture of the oral solution described herein is cherry flavor (e.g., cherry flavor, natural & artificial).

As used herein, "solvent" refers to a liquid substance capable of effectively dissolving and/or dispersing the active ingredient atomoxetine, or pharmaceutically acceptable salt thereof, and the excipients present in the oral solution described herein. Solvents suitable in the manufacture of the oral solution described herein include purified water, propylene glycol, and glycerin.

As used herein, "citric acid anhydrous" refers to citric acid that is substantially water-free. Citric acid refers to the compound with the chemical name 2-hydroxypropane-1,2,3-tricarboxylic acid; CAS number 77-92-9; chemical formula $C_6H_8O_7$; and molar mass 192.123 g·mol$^{-1}$. Citric acid anhydrous has the FDA unique ingredient identifier (UNII) XF417D3PSL.

As used herein, "sucralose" refers to an artificial sweetener and sugar substitute with the chemical name 1,6-dichloro-1,6-dideoxy-β-D-fructofuranosyl 4-chloro-4-deoxy-α-D-galactopyranoside: CAS number 56038-13-2; chemical formula $C_{12}H_{19}Cl_3O_9$; and molar mass 397.64 g·mol$^{-1}$. Sucralose has the FDA unique ingredient identifier (UNII) 96K6UQ3ZD4.

As used herein, "sorbitol" refers to the compound with the chemical name (2S,3R,4R,5R)-hexane-1,2,3,4,5,6-hexol; CAS number 50-70-4; chemical formula $C_6H_{14}O_6$; and molar mass 182.17 g·mol$^{-1}$. Sorbitol has the FDA unique ingredient identifier (UNII) 506T60A25R.

As used herein, "sorbitol solution 70 percent" refers to a liquid solution containing 70% (w/v) sorbitol. Sorbitol solution, 70 percent has the FDA unique ingredient identifier (UNII) 8KW3E207O2.

As used herein, "sodium benzoate powder" refers to sodium benzoate in a powder form. Sodium benzoate has the CAS number 532-32-1; chemical formula C7H5NaO2; and molar mass 144.105 g mol$^{-1}$. Sodium benzoate, powder has the FDA unique ingredient identifier (UNII) OJ245FE5EU.

As used herein, "methylparaben powder" refers to methylparaben in a powder form. Methylparaben has the chemical name methyl 4-hydroxybenzoate; CAS number 99-76-3; chemical formula C8H8O3; and molar mass 152.149 g·mol$^{-1}$. Methylparaben, powder has the FDA unique ingredient identifier (UNII) A218C7HI9T.

As used herein, "trisodium citrate" or "sodium citrate" refers to the compound with the chemical name trisodium 2-hydroxypropane-1,2,3-tricarboxylate; CAS number 68-04-2 (6132-04-3 as the dihydrate); chemical formula Na3C6H5O7; and molar mass 258.06 g/mol (anhydrous) and 294.10 g/mol (dihydrate). Trisodium citrate has the FDA unique ingredient identifier (UNII) RS7A450LGA and B22547B95K (dihydrate).

As used herein, "propylene glycol" refers to the compound with the name propane-1,2-diol; CAS number 57-55-6; chemical formula C3H802; and molar mass 76.095 g·mol$^{-1}$. Propylene glycol has the FDA unique ingredient identifier (UNII) 6DC9Q167V3.

As used herein, "glycerin" refers to the compound with the chemical name propane-1,2,3-triol; CAS number 56-81-5; chemical formula C3H8O3; and molar mass 92.094 g mol$^{-1}$. Glycerin has the FDA unique ingredient identifier (UNII) PDC6A3C0OX.

The term "oral solution" refers to the oral liquid dosage form in which the active ingredient is mixed with a liquid, while being dissolved. The active ingredient particles are substantially dissolved in the liquid. Typically, oral solutions are intended for enteral delivery by orally administering, with or without food.

The term "treating" (and equivalent terms such as "treat," "treated," and "treatment") of a subject includes the administration of an active pharmaceutical ingredient (API), or a unit dosage form containing the same (e.g., oral solution), to a subject with the purpose of preventing, mitigating, curing, healing, alleviating, relieving, altering, remedying, ameliorating, improving, stabilizing or affecting a disease or disorder, or a symptom of the disease or disorder. The disease or disorder can be, e.g., attention deficit hyperactivity disorder (ADHD).

The term "attention deficit hyperactivity disorder" or "ADHD" refers to a neurodevelopmental disorder characterized by excessive amounts of inattention, hyperactivity, and impulsivity that are pervasive, impairing in multiple contexts, and otherwise age-inappropriate. ADHD symptoms arise from executive dysfunction, and emotional dysregulation is often considered a core symptom. In children, problems paying attention may result in poor school performance. ADHD is associated with other neurodevelopmental and mental disorders as well as some non-psychiatric disorders, which can cause additional impairment, especially in modern society. Although people with ADHD struggle to focus on tasks they are not particularly interested in completing, they are often able to maintain an unusually prolonged and intense level of attention for tasks they do find interesting or rewarding; this is known as hyperfocus. ADHD is divided into three primary presentations: (1) predominantly inattentive (ADHD-PI or ADHD-I), (2) predominantly hyperactive-impulsive (ADHD-PH or ADHD-HI), and (3) combined type (ADHD-C).

The term "oral administration" or "PO" refers to a route of administration where a substance is taken through the mouth. Many medications are taken orally because they are intended to have a systemic effect, reaching different parts of the body via the bloodstream.

The oral solution dosage form provided for herein may be prepared, e.g., by contacting the ingredient(s) with a solvent. In doing so, any one or more of the ingredients employed (active ingredient and/or excipients) can effectively be dissolved, suspended, or dispersed therein (e.g., in the solvent). This includes, e.g., salts, solvates, hydrates, dihydrates, monohydrates, powders, microcrystalline forms, crystalline forms, amorphous forms, specified particle size distribution (PSD), etc. of the ingredients. In doing so, the ingredient would therefore no longer necessarily retain that form. However, within the context of the present invention, it is appreciated that those of skill in the art understand and agree that reference to the resulting dosage form as containing ingredients in the indicated form is otherwise acceptable and appropriate.

Additionally, within the context of the present invention, it is appreciated that those of skill in the art understand and agree that reference to the oral solution dosage form as containing the ingredients having a specified state is acceptable and appropriate. This is so, even though those ingredients may no longer necessarily exist in the same state (as specifically indicated) as when introduced to the solvent. Likewise, within the context of the present invention, reference can also be made to the dosage form as being manufactured from (or as being formed from) the ingredients, as specifically indicated. It is appreciated that those of skill in the art understand and agree that each of the above characterizations of the dosage form are acceptable and appropriate.

For example, within the context of the oral solution dosage form, reference to "atomoxetine hydrochloride" is also a reference to atomoxetine as the free base. Within the context of the oral solution dosage form, reference to "citric acid anhydrous" is also a reference to citric acid. Within the context of the oral solution dosage form, reference to "sorbitol solution, 70 percent" is also a reference to sorbitol. Within the context of the oral solution dosage form, reference to "sodium saccharin" or "saccharin sodium, dihydrate, powder" is also a reference to saccharin. Within the context of the oral solution dosage form, reference to "sodium benzoate, powder" is also a reference to benzoic acid and/or sodium benzoate. Within the context of the oral solution dosage form, reference to "methylparaben, powder" is also a reference to methylparaben. Within the context of the oral solution dosage form, reference to "trisodium citrate anhydrous" is also a reference to trisodium citrate.

SPECIFIC EMBODIMENTS

The specific embodiments provided below are for illustration purposes only, and do not otherwise limit the scope of the disclosed subject matter, as defined by the claims.

In specific embodiments, the atomoxetine oral solution is indicated for the treatment of Attention-Deficit/Hyperactivity Disorder (ADHD).

In specific embodiments, the atomoxetine present in the atomoxetine oral solution has the following initial, target, and/or maximum daily dose:

| Body Weight | Initial Daily Dose | Target Total Daily Dose | Maximum Total Daily Dose |
|---|---|---|---|
| Children and adolescents up to 70 kg | 0.5 mg/kg | 1.2 mg/kg | 1.4 mg/kg |
| Children and adolescents over 70 kg and adults | 40 mg | 80 mg | 100 mg |

In specific embodiments, the atomoxetine oral solution is administered such that atomoxetine, or a pharmaceutically acceptable salt thereof, is orally administered, equivalent to up to 100 mg atomoxetine free base.

In specific embodiments, the atomoxetine oral solution is administered such that atomoxetine, or a pharmaceutically acceptable salt thereof, is orally administered, equivalent to at least 10 mg atomoxetine free base.

In specific embodiments, the atomoxetine oral solution is administered such that atomoxetine, or a pharmaceutically acceptable salt thereof, is orally administered, equivalent to 10-100 mg atomoxetine free base.

In specific embodiments, the atomoxetine oral solution is administered such that atomoxetine, or a pharmaceutically acceptable salt thereof, is orally administered, equivalent to 10 mg, 18 mg, 25 mg, 40 mg, 60 mg, 80 mg, or 100 mg atomoxetine free base.

In specific embodiments, the atomoxetine oral solution is administered for the treatment of Attention-Deficit/Hyperactivity Disorder (ADHD).

In specific embodiments, the atomoxetine oral solution is administered for the acute treatment of Attention-Deficit/Hyperactivity Disorder (ADHD).

In specific embodiments, the atomoxetine oral solution is administered for the acute treatment of Attention-Deficit/Hyperactivity Disorder (ADHD) in children and adolescents up to 70 kg body weight. In such embodiments, the atomoxetine is initiated at a total daily dose of approximately 0.5 mg/kg and increased after a minimum of 3 days to a target total daily dose of approximately 1.2 mg/kg administered either as a single daily dose in the morning or as evenly divided doses in the morning and late afternoon/early evening. In such embodiments, the total daily dose in children and adolescents should not exceed 1.4 mg/kg or 100 mg, whichever is less.

In specific embodiments, the atomoxetine oral solution is administered for the acute treatment of Attention-Deficit/Hyperactivity Disorder (ADHD) in children and adolescents over 70 kg body weight. In such embodiments, the atomoxetine is initiated at a total daily dose of 40 mg and increased after a minimum of 3 days to a target total daily dose of approximately 80 mg administered either as a single daily dose in the morning or as evenly divided doses in the morning and late afternoon/early evening. After 2 to 4 additional weeks, the dose may be increased to a maximum of 100 mg in patients who have not achieved an optimal response. In such embodiments, the maximum total daily dose in children and adolescents over 70 kg and adults is 100 mg.

In specific embodiments, the atomoxetine oral solution is administered for the maintenance/extended treatment of Attention-Deficit/Hyperactivity Disorder (ADHD).

In specific embodiments, the atomoxetine oral solution is administered for the maintenance/extended treatment for pediatric patients (ages 6-15 years) with Attention-Deficit/Hyperactivity Disorder (ADHD), wherein the atomoxetine is administered at a total daily dose of 1.2 to 1.8 mg/kg/day, administered either as a single daily dose in the morning or as evenly divided doses in the morning and late afternoon/early evening.

In specific embodiments, the atomoxetine oral solution is taken with or without food.

In specific embodiments, the atomoxetine oral solution is taken with food.

In specific embodiments, the atomoxetine oral solution is taken without food.

In specific embodiments, the atomoxetine oral solution is discontinued without being tapered.

In specific embodiments, the atomoxetine oral solution includes atomoxetine, or pharmaceutically acceptable salt thereof, in 10.5±2 mg/mL.

In specific embodiments, the atomoxetine oral solution includes atomoxetine, or pharmaceutically acceptable salt thereof, in 10.5±1 mg/mL.

In specific embodiments, the atomoxetine oral solution includes atomoxetine, or pharmaceutically acceptable salt thereof, in 10.5±0.5 mg/mL.

In specific embodiments, the atomoxetine oral solution includes atomoxetine, or pharmaceutically acceptable salt thereof, in 11.43±2 mg/mL as the hydrochloride salt.

In specific embodiments, the atomoxetine oral solution includes atomoxetine, or pharmaceutically acceptable salt thereof, in 11.43±1 mg/mL as the hydrochloride salt.

In specific embodiments, the atomoxetine oral solution includes atomoxetine, or pharmaceutically acceptable salt thereof, in 11.43±0.5 mg/mL as the hydrochloride salt.

In specific embodiments, the atomoxetine oral solution includes atomoxetine, or pharmaceutically acceptable salt thereof, in 10±2 mg/mL as the free base.

In specific embodiments, the atomoxetine oral solution includes atomoxetine, or pharmaceutically acceptable salt thereof, in 10±1 mg/mL as the free base.

In specific embodiments, the atomoxetine oral solution includes atomoxetine, or pharmaceutically acceptable salt thereof, in 10±0.5 mg/mL as the free base.

In specific embodiments, the atomoxetine oral solution is manufactured from atomoxetine, as the hydrochloride salt.

In specific embodiments, the atomoxetine oral solution is manufactured from atomoxetine, as the free base.

In specific embodiments, the atomoxetine oral solution includes the antimicrobial preservative in 2±0.4 mg/mL.

In specific embodiments, the atomoxetine oral solution includes the antimicrobial preservative in 2±0.2 mg/mL.

In specific embodiments, the atomoxetine oral solution includes the antimicrobial preservative in 2±0.1 mg/mL.

In specific embodiments, the atomoxetine oral solution includes methylparaben in 1±0.2 mg/mL.

In specific embodiments, the atomoxetine oral solution includes methylparaben in 1±0.1 mg/mL.

In specific embodiments, the atomoxetine oral solution includes methylparaben in 1±0.05 mg/mL.

In specific embodiments, the atomoxetine oral solution includes sodium benzoate in 1±0.2 mg/mL.

In specific embodiments, the atomoxetine oral solution includes sodium benzoate in 1±0.1 mg/mL.

In specific embodiments, the atomoxetine oral solution includes sodium benzoate in 1±0.05 mg/mL.

In specific embodiments, the atomoxetine oral solution is manufactured from sodium benzoate, as sodium benzoate, powder.

In specific embodiments, the atomoxetine oral solution includes the buffering agent in 2.84±0.5 mg/mL.

In specific embodiments, the atomoxetine oral solution includes the buffering agent in 2.84±0.25 mg/mL.

In specific embodiments, the atomoxetine oral solution includes the buffering agent in 2.84±0.125 mg/mL.

In specific embodiments, the atomoxetine oral solution includes citric acid in 1.50±0.3 mg/mL.

In specific embodiments, the atomoxetine oral solution includes citric acid in 1.50±0.15 mg/mL.

In specific embodiments, the atomoxetine oral solution includes citric acid in 1.50±0.075 mg/mL.

In specific embodiments, the atomoxetine oral solution is manufactured from citric acid, as anhydrous citric acid.

In specific embodiments, the atomoxetine oral solution includes trisodium citrate in 1.34±0.27 mg/mL.

In specific embodiments, the atomoxetine oral solution includes trisodium citrate in 1.34±0.1 mg/mL.

In specific embodiments, the atomoxetine oral solution includes trisodium citrate in 1.34±0.05 mg/mL.

In specific embodiments, the atomoxetine oral solution is manufactured from trisodium citrate, as trisodium citrate dihydrate.

In specific embodiments, the atomoxetine oral solution includes the sweetening agent in 57.25±10 mg/mL.

In specific embodiments, the atomoxetine oral solution includes the sweetening agent in 57.25±5 mg/mL.

In specific embodiments, the atomoxetine oral solution includes the sweetening agent in 57.25±2.5 mg/mL.

In specific embodiments, the atomoxetine oral solution includes sucralose in 1±0.2 mg/mL.

In specific embodiments, the atomoxetine oral solution includes sucralose in 1±0.1 mg/mL.

In specific embodiments, the atomoxetine oral solution includes sucralose in 1±0.05 mg/mL.

In specific embodiments, the atomoxetine oral solution includes sorbitol in 56.25±10 mg/mL.

In specific embodiments, the atomoxetine oral solution includes sorbitol in 56.25±5 mg/mL.

In specific embodiments, the atomoxetine oral solution includes sorbitol in 56.25±2.5 mg/mL.

In specific embodiments, the atomoxetine oral solution is manufactured from sorbitol, as sorbitol, 70 percent solution.

In specific embodiments, the atomoxetine oral solution includes the solvent in 906.7±50 mg/mL.

In specific embodiments, the atomoxetine oral solution includes the solvent in 906.7±25 mg/mL.

In specific embodiments, the atomoxetine oral solution includes the solvent in 906.7±12.5 mg/mL.

In specific embodiments, the atomoxetine oral solution includes water in 811.70±50 mg/mL.

In specific embodiments, the atomoxetine oral solution includes water in 811.70±25 mg/mL.

In specific embodiments, the atomoxetine oral solution includes water in 811.70±12.5 mg/mL.

In specific embodiments, the atomoxetine oral solution includes propylene glycol in 20±4 mg/mL.

In specific embodiments, the atomoxetine oral solution includes propylene glycol in 20±2 mg/mL.

In specific embodiments, the atomoxetine oral solution includes propylene glycol in 20±1 mg/mL.

In specific embodiments, the atomoxetine oral solution includes glycerin in 75±15 mg/mL.

In specific embodiments, the atomoxetine oral solution includes glycerin in 75±7.5 mg/mL.

In specific embodiments, the atomoxetine oral solution includes glycerin in 75±3.75 mg/mL.

In specific embodiments, the atomoxetine oral solution includes the flavoring agent in 2±0.4 mg/mL.

In specific embodiments, the atomoxetine oral solution includes the flavoring agent in 2±0.2 mg/mL.

In specific embodiments, the atomoxetine oral solution includes the flavoring agent in 2±0.1 mg/mL.

In specific embodiments, the atomoxetine oral solution includes the coloring agent in 0.002±0.0004 mg/mL.

In specific embodiments, the atomoxetine oral solution includes the coloring agent in 0.002±0.0002 mg/mL.

In specific embodiments, the atomoxetine oral solution includes the coloring agent in 0.002±0.0001 mg/mL.

In specific embodiments, the atomoxetine oral solution includes: (i) 11.43±3 mg/mL atomoxetine hydrochloride; (ii) antimicrobial preservative that includes 1±0.2 mg/mL methylparaben and 1±0.2 mg/mL sodium benzoate; (iii) buffering agent that includes 1.50±0.3 mg/mL citric acid and 1.34±0.27 mg/mL trisodium citrate dihydrate; (iv) sweetening agent that includes 1±0.2 mg/mL sucralose and 56.25±11 mg/mL sorbitol; (v) solvent that includes 811.70±50 mg/mL water, 20±4 mg/mL propylene glycol, and 75±15 mg/mL glycerin; (vi) flavoring agent that includes 2±0.4 mg/mL cherry flavor; and (vii) coloring agent that includes 0.001±0.0002 mg/mL FD & C Red No. 40 and 0.001±0.0002 mg/mL Allura Red AC.

In specific embodiments, the atomoxetine oral solution includes: (i) 11.43±1.5 mg/mL atomoxetine hydrochloride; (ii) antimicrobial preservative that includes 1±0.1 mg/mL methylparaben and 1±0.1 mg/mL sodium benzoate; (iii) buffering agent that includes 1.50±0.15 mg/mL citric acid and 1.34±0.1 mg/mL trisodium citrate dihydrate; (iv) sweetening agent that includes 1±0.1 mg/mL sucralose and 56.25±5 mg/mL sorbitol; (v) solvent that includes 811.70±25 mg/mL water, 20±2 mg/mL propylene glycol, and 75±7.5 mg/mL glycerin; (vi) flavoring agent that includes 2±0.2 mg/mL cherry flavor; and (vii) coloring agent that includes 0.001±0.0001 mg/mL FD & C Red No. 40 and 0.001±0.0001 mg/mL Allura Red AC.

In specific embodiments, the atomoxetine oral solution is administered to an adult, at least 18 years old.

In specific embodiments, the atomoxetine oral solution is administered to a child, less than 18 years old.

In specific embodiments, the atomoxetine oral solution is administered to a child, age 6-15 years.

In specific embodiments, the atomoxetine oral solution is administered to treat attention deficit hyperactivity disorder (ADHD).

In specific embodiments, administration of the atomoxetine oral solution provides for an enhancement in cognitive performance.

In specific embodiments, administration of the atomoxetine oral solution provides for an enhancement in cognitive performance, including at least one of improved alertness, improved attention, and improved memory.

In specific embodiments, the atomoxetine oral solution is packaged in a container.

In specific embodiments, the atomoxetine oral solution is packaged in an amber colored polyethylene terephthalate (PET) bottle.

In specific embodiments, the atomoxetine oral solution is packaged in a glass bottle.

In specific embodiments, the atomoxetine oral solution is packaged in a high-density polyethylene (HDPE) bottle.

In specific embodiments, the atomoxetine oral solution is packaged in a low-density polyethylene (LDPE) bottle.

In specific embodiments, the atomoxetine oral solution is packaged in a polypropylene (PP) bottle.

In specific embodiments, the atomoxetine oral solution is packaged in a glass or plastic bottle with a child proof closure.

In specific embodiments, the atomoxetine oral solution is packaged in a glass or plastic bottle and the packaging further includes a syringe or cup, marked in mL, ounces, or both.

In specific embodiments, the atomoxetine oral solution is packaged in a glass or plastic bottle configured for use to administer multiple doses of topiramate.

In specific embodiments, the atomoxetine oral solution, while packaged in a container, is free from microbial contamination for a specified period of time (e.g., ≥20 days, ≥30 days, ≥60 days, ≥90 days, ≥180 days, ≥12 months, or ≥24 months) when tested according to <1111>USP-30 NF-25.

In specific embodiments, the atomoxetine oral solution, while packaged in a container, is free from microbial contamination for an extended period of time encountered with the shipping and storage of the atomoxetine oral solution.

In specific embodiments, the atomoxetine oral solution, while packaged in a container, is free from microbial contamination for an extended period of time encountered with the shipping and storage of the atomoxetine oral solution under ambient conditions, wherein the microbial contamination includes *Escherichia coli* (*E. coli*).

In specific embodiments, the atomoxetine oral solution, while packaged in a container, is free from microbial contamination for an extended period of time encountered with the shipping and storage of the atomoxetine oral solution under ambient conditions, wherein the microbial contamination includes less than 0.1 wt. % *Escherichia coli* (*E. coli*).

In specific embodiments, the atomoxetine oral solution, while packaged in a container, is free from microbial contamination for an extended period of time encountered with the shipping and storage of the atomoxetine oral solution under ambient conditions, wherein the microbial contamination includes less than 0.05 wt. % *Escherichia coli* (*E. coli*).

In specific embodiments, the atomoxetine oral solution, while packaged in a container, is free from microbial contamination for an extended period of time encountered with the shipping and storage of the atomoxetine oral solution under ambient conditions, wherein the microbial contamination includes less than 0.01 wt. % *Escherichia coli* (*E. coli*).

In specific embodiments, the atomoxetine oral solution, while packaged in a container, is free from microbial contamination for an extended period of time encountered with the shipping and storage of the atomoxetine oral solution under ambient conditions, wherein the microbial contamination includes *Burkholderia cepacia* complex (BCC).

In specific embodiments, the atomoxetine oral solution, while packaged in a container, is free from microbial contamination for an extended period of time encountered with the shipping and storage of the atomoxetine oral solution under ambient conditions, wherein the microbial contamination includes less than 0.1 wt. % *Burkholderia cepacia* complex (BCC).

In specific embodiments, the atomoxetine oral solution, while packaged in a container, is free from microbial contamination for an extended period of time encountered with the shipping and storage of the atomoxetine oral solution under ambient conditions, wherein the microbial contamination includes less than 0.05 wt. % *Burkholderia cepacia* complex (BCC).

In specific embodiments, the atomoxetine oral solution, while packaged in a container, is free from microbial contamination for an extended period of time encountered with the shipping and storage of the atomoxetine oral solution under ambient conditions, wherein the microbial contamination includes less than 0.01 wt. % *Burkholderia cepacia* complex (BCC).

In specific embodiments, the atomoxetine oral solution, while packaged in a container, is free from microbial contamination for at least 24 months under ambient conditions.

In specific embodiments, the atomoxetine oral solution, while packaged in a container, is free from microbial contamination for at least 12 months under ambient conditions.

In specific embodiments, the atomoxetine oral solution, while packaged in a container, is free from microbial contamination for at least 6 months under ambient conditions.

In specific embodiments, the atomoxetine oral solution, while packaged in a container, is free from microbial contamination for at least 180 days under ambient conditions.

In specific embodiments, the atomoxetine oral solution, while packaged in a container, is free from microbial contamination for at least 90 days under ambient conditions.

In specific embodiments, the atomoxetine oral solution is an immediate release dosage form.

The invention claimed is:

1. An oral solution comprising:

(i) atomoxetine hydrochloride in an amount of 11.43±3 mg/ml;

(ii) antimicrobial preservative comprising methylparaben and sodium benzoate;

(iii) buffering agent comprising citric acid and trisodium citrate dihydrate;

(iv) sweetening agent comprising sucralose and sorbitol;

(v) solvent comprising water, propylene glycol, and glycerin;

(vi) optionally flavoring agent comprising cherry flavor; and (vii) optionally coloring agent comprising FD & C Red No. 40.

2. The oral solution of claim 1, wherein the atomoxetine hydrochloride is present at 11.43±2 mg/mL.

3. The oral solution of claim 1, wherein the antimicrobial preservative is present in 2±0.4 mg/mL.

4. The oral solution of claim 1, wherein the methylparaben is present in 1±0.2 mg/mL.

5. The oral solution of claim 1, wherein the sodium benzoate is present in 1±0.2 mg/mL.

6. The oral solution of claim 1, wherein the buffering agent is present in 2.84±0.5 mg/mL.

7. The oral solution of claim 1, wherein the citric acid is present in 1.50±0.3 mg/mL.

8. The oral solution of claim 1, wherein the trisodium citrate is present in 1.34±0.27 mg/mL.

9. The oral solution of claim 1, wherein the sweetening agent is present in 57.25±10 mg/mL.

10. The oral solution of claim 1, wherein the sucralose is present in 1±0.2 mg/mL.

11. The oral solution of claim 1, wherein the sorbitol is present in 56.25±10 mg/mL.

12. The oral solution of claim 1, wherein the solvent is present in 906.7±50 mg/mL.

13. The oral solution of claim 1, wherein the water is present in 811.70±50 mg/mL.

14. The oral solution of claim 1, wherein the propylene glycol is present in 20±4 mg/mL.

15. The oral solution of claim 1, wherein the glycerin is present in 75±15 mg/mL.

16. The oral solution of claim 1, wherein the flavoring agent is present in 2±0.4 mg/mL.

17. The oral solution of claim 1, wherein the coloring agent is present in 0.002±0.0004 mg/mL.

18. An oral solution comprising:

(i) 11.43±3 mg/mL atomoxetine hydrochloride;

(ii) antimicrobial preservative comprising 1±0.2 mg/mL methylparaben and 1±0.2 mg/mL sodium benzoate;

(iii) buffering agent comprising 1.50±0.3 mg/mL citric acid and 1.34±0.27 mg/mL trisodium citrate dihydrate;

(iv) sweetening agent comprising 1±0.2 mg/mL sucralose and 56.25±11 mg/mL sorbitol;

(v) solvent comprising 811.70±50 mg/mL water, 20±4 mg/mL propylene glycol, and 75±15 mg/mL glycerin;

(vi) flavoring agent comprising 2±0.4 mg/mL cherry flavor; and (vii) coloring agent comprising 0.001±0.0002 mg/mL FD & C Red No. 40.

19. A method of treating attention deficit hyperactivity disorder (ADHD) in a human subject, the method comprising orally administering the oral solution of claim 18 to a human subject in need thereof, in an amount and for a period of time sufficient to treat the ADHD.

20. The method of claim 19, further comprising the administration of a psychostimulant.

21. The method of claim 19, wherein the administration further provides for an enhancement in cognitive performance, including at least one of improved alertness, improved attention, and improved memory.

* * * * *